United States Patent [19]

Ishikawa et al.

[11] Patent Number: 4,487,069
[45] Date of Patent: Dec. 11, 1984

[54] METHOD OF IMAGE DISPLAY BY ULTRASONIC MICROSCOPE

[75] Inventors: Isao Ishikawa, Hino; Hiroshi Kanda, Tokorozawa, both of Japan

[73] Assignee: Hitachi, Ltd., Tokyo, Japan

[21] Appl. No.: 519,743

[22] Filed: Aug. 2, 1983

[30] Foreign Application Priority Data

Sep. 20, 1982 [JP] Japan ............... 57-164499

[51] Int. Cl.³ ............................. G01N 29/04
[52] U.S. Cl. ........................ 73/606; 73/633; 73/810
[58] Field of Search ............ 73/606, 633, 810, 821, 73/834

[56] References Cited

U.S. PATENT DOCUMENTS 4,430,897  2/1984  Quate ................................ 73/606
4,442,714  4/1984  Bongianni ........................ 73/606

Primary Examiner—Howard A. Birmiel
Attorney, Agent, or Firm—Antonelli, Terry & Wands

[57] ABSTRACT

A method of image display of a specimen by an ultrasonic wave microscope comprising an acoustic wave propagating medium, a piezoelectric member provided at one end of said medium for generating an ultrasonic beam, and an acoustic wave lens formed at an opposite end of said acoustic wave propagating medium and having a predetermined focal point, said method comprising the steps of two-dimensionally scanning a specimen disposed substantially at said focal point by said ultrasonic beam while moving one of said specimen and said beam relative to the other, and applied to said specimen repetitive stress selectively during the scanning of said specimen.

3 Claims, 11 Drawing Figures

METHOD OF IMAGE DISPLAY BY ULTRASONIC MICROSCOPE The present invention relates to a method of image display by ultrasonic microscope, or more in particular to a method of image display by ultrasonic microscope for observing the fatigue failure or tensile rupture of a specimen.

In recent years, the generation and detection of an acoustic wave of an ultrahigh frequency as high as 1 GHz has been made possible. This has led to the realization of an acoustic wave of about 1 μm under water, thereby making available an acoustic wave image-display device of high resolution. Specifically, a converged acoustic beam is produced by use of a concave lens to realize a resolution as high as 1 μm. A specimen is located in the path of this beam and the ultrasonic wave reflected from the specimen is detected, so that the elastic property of the microstructure of the specimen is examined. By scanning the specimen two-dimensionally in mechanical manner and displaying the intensity of reflected signal as a luminance signal on a CRT display unit, the microstructure of the specimen can be observed in magnified form.

FIG. 1 shows the essential parts of a conventional ultrasonic microscope and FIGS. 2a to 2c are diagrams for explaining the operation of the microscope of FIG. 1.

The convergence and transmission/receiving of the ultrasonic wave are effected by a spherical lens comprising an acoustic wave propagating medium 1 of a cylindrical molten quartz or the like with one side thereof optically polished, a piezoelectric thin film 2 such as $(ZnO)_2$ disposed on the surface medium 1, and upper and lower electrodes 3 sandwiching the piezoelectric thin film 2. The piezoelectric thin film 2 is impressed with an electric pulse signal 5 generated from a pulse oscillator 4 thereby to generate an ultrasonic acoustic wave 6. The opposite side of the sound wave propagating medium 1 has a hemispherical recess L approximately 0.1 mm to 1.0 mm in diameter. A medium such as water 8 for propagating the ultrasonic wave 6 to the specimen 7 is filled between the hemispherical recess L and a specimen 7 disposed on a table 14. The ultrasonic wave 6 generated by the piezoelectric thin film 2 propagates through the medium 1 as a plane wave. When the plane wave reaches the hemispherical recess L, refraction (lens action) occurs by the difference between propagating velocity of acoustic wave in the quartz (6000 m/s) and that in the water (1500 m/s), thus making it possible to radiate the converged ultrasonic wave 6 on the specimen 7. The ultrasonic wave reflected from the specimen 7, is converged and regulated in phase by the spherical lens and reaches the piezoelectric thin film 2 in the form of plane wave. The ultrasonic wave is converted by the thin film 2 into a radio frequency signal 9. This radio frequency signal 9 is received by a receiver 10, where after it is converted by diode-detection into a video signal 11, which is applied to a CRT display unit 12.

As shown in FIG. 2a, a train of pulses 5 generated from the pulse oscillator 4 are first observed on the screen of the CRT display unit 12, and then a radio frequency pulse signal 16 reflected by the boundary between the hemispherical recess L and the medium 8 appears, followed by an RF signal 9 reflected from the specimen after the lapse of a predetermined period of time. The pulse oscillator 4 periodically generates the pulses 5' with a period T of each cycle, so that reflected waves 16' and 9' are displayed repeatedly. Actually, the signals generated before time point $t_1$ shown by dotted line are cut off by a gate means, and therefore the waves 16, 16' reflected by the boundary between the recess and the medium 8 are not displayed on the screen.

In the apparatus of FIG. 1, the specimen 7 is scanned two-dimensionally in the plane X-Y by driving the table 14 by a specimen table drive power source 13. More specifically, the table is first positioned such that the wave beam is first reflected at a point of the specimen 7 represented by (x=1; y=1) as shown in FIG. 2. Then, the table 14 is moved in the X-direction so that the wave is reflected at a point (x=2; y=1) of the specimen 7 (for X-direction scanning). In this way, the specimen is moved in X-direction, so that the points (x=1, 2, 3,—; y=1) of the specimen 7 are sequentially scanned by the wave beam. After completion of the X-direction along the line of y=1, the table is reversely moved in the X-direction and also forwardly in the Y-direction (Y-direction scanning so that the next X-direction scanning begins at a point (x=1; y=2) of the specimen. In this manner, a multiplicity of points (say, 512 points) of the specimen 7 are scanned two-dimensionally and the variation of intensity of reflection from the specimen surface is displayed two-dimensionally on the screen of the CRT display unit 12 whose scanning lines are driven two-dimensionally in synchronism with the X-direction and Y-direction scannings of the specimen 7. On the surface of the specimen 7 shown in FIG. 2b, for example, numerals 17 and 18 indicate hard surface portions where reflection intensity is high, and the remaining portion is a soft surface where reflection intensity is low.

Generally, only a part of the ultrasonic wave is reflected from the surface of an object, and a substantial portion thereof penetrates into the object regardless of whether the object is optically transparent or not, and returns as an echo representing the variations of hardness, density or viscosity or flaws, if any, within the material of the object. The ultasonic microscope, which takes advantage of this characteristic, is to form an image indicative of the conditions inside of the specimen 7. Further, there is a current demand to observe the progress of fatigue of the specimen 7 under ultrasonic microscope by applying repetitive stress to the specimen 7. As an example, the specimen 7 such as the wing of aircraft, the axle of a tram car or a building structure, is preliminarily cut at the central part thereof as designated by numeral 19 in FIG. 2c. Then, the specimen is subjected to a tensile test and a compression test thereby to measure the number of vibrations applied before rupture. In this case, since the specimen 7 is moved for scanning by the specimen table drive power supply 13, it is difficult to simultaneously apply to the specimen repetitive tensile and compression tests while assuring accurate observation of the elasticity, viscosity and density of the surface of the specimen.

Accordingly, the object of the present invention is to provide a method of image display by ultrasonic microscope which solves the above-mentioned problem of the prior art and make possible observation of the processes of fatigue and tensile rupture of a specimen as applying the repetitive stress thereto.

In order to achieve this object, there is provided according to the present invention a method of image display by ultrasonic microscope comprising an acoustic wave propagating medium and an acoustic wave lens formed at the end of the propagating medium and having a predetermined focal point for taking an image of a specimen disposed substantially at the focal point from acoustic wave irregularly reflected from the specimen during scanning thereof, wherein repetitive stress is applied to the specimen selectively during the scanning.

The present invention will be apparent from the following detailed description taken in conjunction with the accompanying drawings, in which.

Figure 3A:
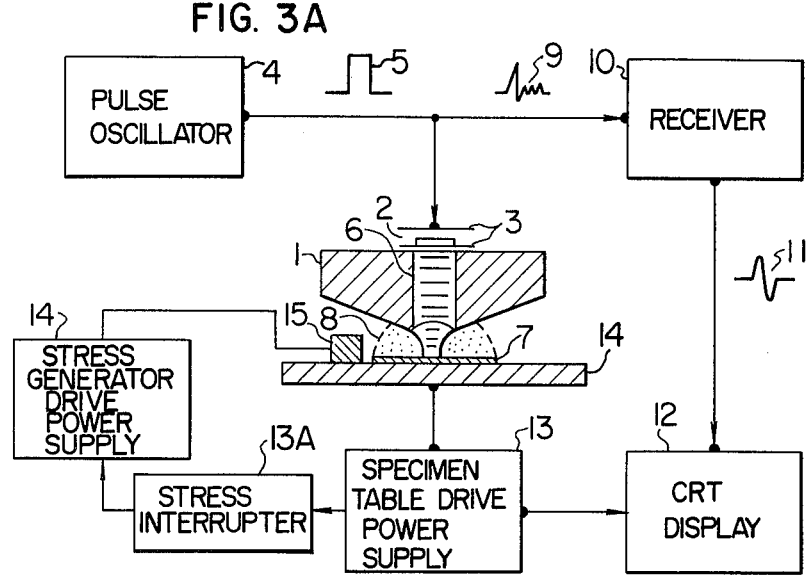
FIGS. 3A and 3B show diagrams showing essential parts of an ultrasonic microscope for performing the method of image display according to the present invention.
Figure 3B:
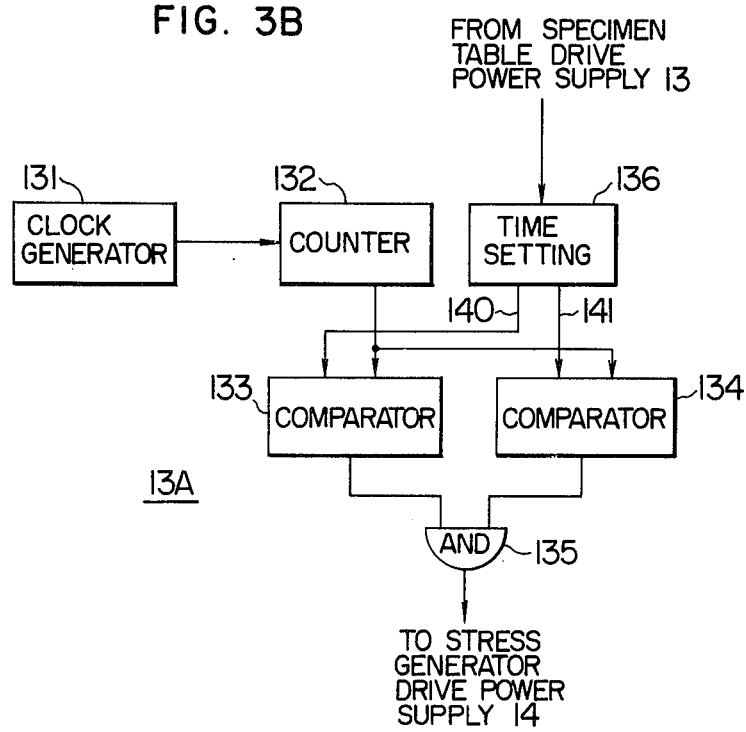

A configuration of an ultrasonic microscope for carrying out the method of image display according to the present invention is shown in FIGS. 3A and 3B.

Figure 1:
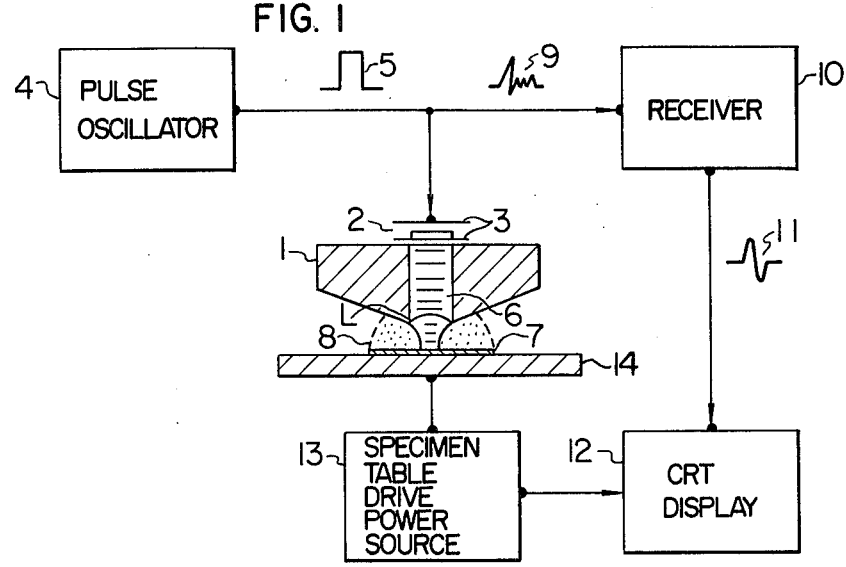
FIG. 1 is a diagram showing the essential parts of a conventional ultrasonic microscope.
Figure 2A:
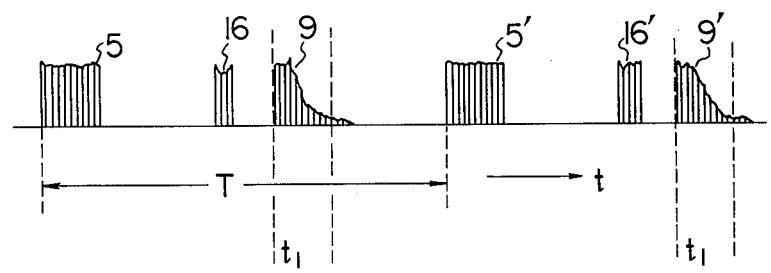
FIGS. 2a and 2b are diagrams for explaining the operation of the apparatus of FIG. 1.
Figure 2B:
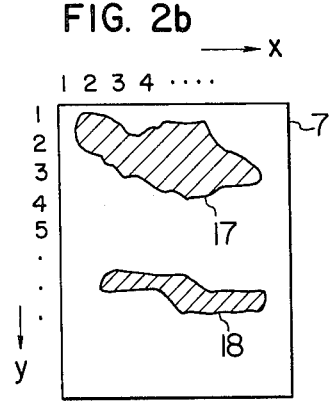
Figure 2C:
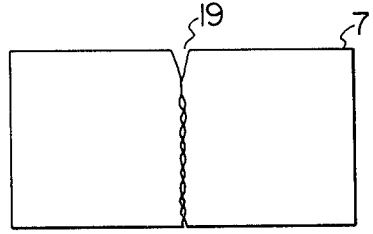

The apparatus of FIGS. 3A and 3B, is different from the apparatus of FIG. 1 in that the former is provided with a stress interrupter 13A, a stress generator drive power supply 14 and a repetitive stress generator 15. Other components are identical to those included in FIG. 1. The drive power supply 14 is for driving the repetitive stress generator 15 according to a scan synchronous signal applied thereto through the stress interrupter 13A from the specimen table drive power supply 13. The drive power supply 14 is capable of driving or stopping the repetitive stress generator 15 only in a specified range in the Y-direction scanning which is controlled by the stress interrupter 13B as mentioned hereinafter.

Figure 4:
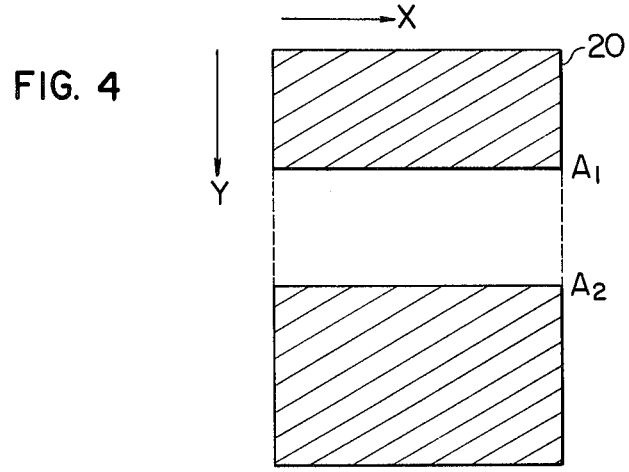
FIG. 4 is a diagram showing a display screen indicating the repetitive stress applied condition according to the present invention.

FIG. 4 shows the repetitive stress applied to the specimen as indicated on the display screen according to the method of image display of the present invention.

In FIG. 4, the specific scanning range, that is, the range of application of repetitive stress is stopped in the range between $A_1$ and $A_2$. Scan of each frame is carried out by repeating scanning along a line in the X-direction (X-direction scan), while shifting the scanning line in the Y-direction (Y-direction scan). The repetitive stress generating power supply 15 is driven or stopped between point $A_1$ and point $A_2$ in the Y-direction scanning. In FIG. 4, assume that the repetetive stress generator 15 is stopped in a range of $A_1$ to $A_2$ during the Y-direction scanning. During this period, the image 20 is maintained unchanged. With this process, a specified range of the image is observed under a condition that no repetitive stress is applied to the specimen 7, while when the scanning is made in other ranges, the repetitive stress is applied to the specimen 7.

Therefore, in the event that a cracking occurs in the material in the progress of fatigue, for instance, and it is desired to observe the relation between the propagation of the front edge of the crack and the repetitive stress, this is achieved by stopping the application of repetitive stress when the Y-direction scanning reaches a point immediately before the crack position and again applying the repetitive stress after passing the crack position so that the condition of the crack position immediately after application of repetitive stress is displayed on the screen 20 during the next scanning of the crack position.

The range of $A_1$ to $A_2$ is controlled by the stress interrupter 13B as shown in FIG. 3B. In the figure, clock pulses produced by a clock generator 131 are applied to a counter 132, whose count value is applied to one input of each of comparators 133 and 134. The other inputs of the comparators 133 and 134 are supplied with outputs 140 and 141, respectively, of a time setting device 136. The outputs 140 and 141 represent count values corresponding to the time periods required for scanning from the top line to the lines $A_1$ and $A_2$, respectively, of the frame as shown in FIG. 4. These count values are produced on the basis of the Y-direction scanning signal supplied from the specimen table drive power supply 13. The comparator 133 produces a high level signal "1" when the count value of the counter 132 exceeds the output 140, while the comparator 134 produces a high level signal "1" when the output 141 is less than the count value of the counter 132. Thus, the outputs of the comparators 133 and 134 are both at high level in a range of $A_1$ to $A_2$ so that an AND gate 135 produces a high level signal "1" in the range of $A_1$ to $A_2$. The stress generator drive power supply is rendered inoperative with the high level signal "1" of the AND gate 135 so that the stress applied to the specimen is stopped in the range of $A_1$ to $A_2$. The stress generator drive power supply may be arranged to be rendered operative with the high level signal "1" of the AND gate 135, if it is desired to apply the stress to the specimen only in the range of $A_1$ to $A_2$.

FIGS. 5a to 5d show various constructions of the repetitive stress generating device employed in the present invention.

Figure 5A:
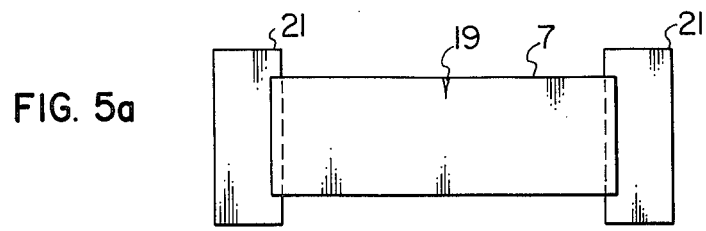
FIGS. 5a to 5d are diagrams showing a construction of a repetitive stress generator for realizing the method of image display according to the present invention.

FIG. 5a is a top plan view of the specimen 7 supported on a pair of supports 21, the specimen 7 having a crack 19 developed previously.

Figure 5B:
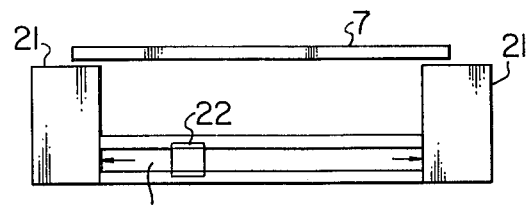

FIG. 5b is a front view of a repetitive stress generating device using a piezoelectric element 22, wherein a voltage is applied from the repetitive stress generating power supply 15 to the piezoelectric element 22 to generate a specific mechanical displacement, and the amount of this displacement is applied to the specimen 7. That is, when the piezoelectric element 22 is displaced outward or inward, the bar 32 disposed between the supports 21 is expanded outward or contracted inward so that the supports 21 move outward or inward. As a result the specimen 7 fixed to the supports 21 is pulled outward or pressed inward thereby to be subjected to tensile stress and compression stress repetitively.

Figure 5C:
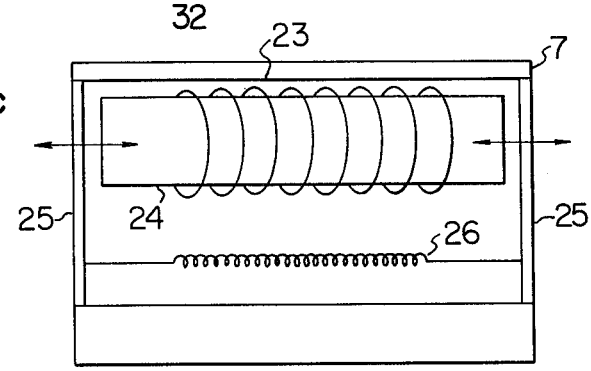

FIG. 5c shows a front view of a repetitive stress application device using electromagnetic force. In FIG. 5c, the AC current is applied from the repetitive stress generating power supply 15 to the electromagnet 23 thereby to oscillate movable pieces 25, with the result that the specimen 7 fixed to the movable pieces 25 is subjected to repetitive tensile stress and compression stress.

Figure 5D:
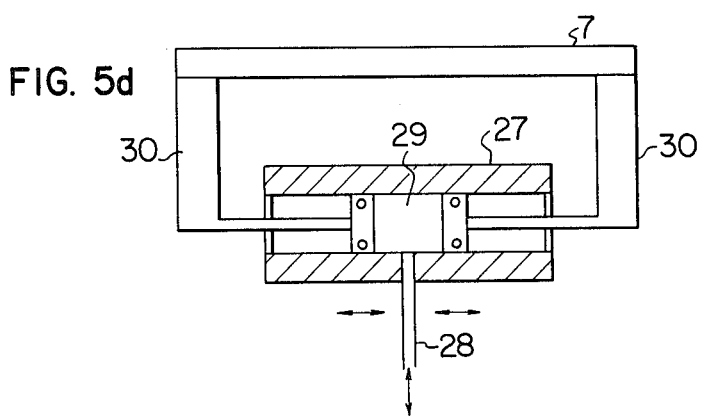

FIG. 5d is a front sectional view of a repetitive stress application device employing oil pressure.

By charging and discharging the oil 29 by way of a pipe 28 of a piston 27, supporting rods 30 move outward and inward respectively thereby to apply the tensile stress and compression stress repetitively to the specimen 7.

Figure 6:
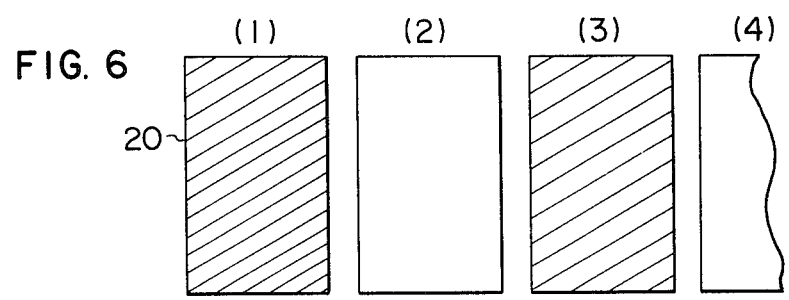
FIG. 6 is a diagram showing a display screen for indicating the repetitive stress applied condition according to another method of image display of the present invention.

FIG. 6 shows successive frames in scanning to be displayed on a display screen when repetitive stress is applied according to another embodiment of the present invention.

The mode of FIG. 4 is suitable when the scanning speed is not so high. In the case where the scanning speed is as high as 30 to 40 seconds per frame such as the electronic scanning, however, one or more frames may be produced with application of repetitive stress and the next frame is scanned with application of no stress thereby producing a still image.

In FIG. 6, the hatched frames (1), (3),—and so on represent the ones produced with application of repetitive stress, while the blank frames (2), (4),—and so on indicate still images. Since the repetitive stress is exerted on the specimen 7 during scanning of the frames of (1), (3),—and so on, the results from application of repetitive stress are observed during scanning of the frames (2), (4),—and so on, thus making it possible to form an image showing in detail the process of any fatigue or tensile rupture that may occur.

It will be readily understood that the operation mode of FIG. 6 can be carried out by adjusting the outputs 140 and 141 of the time setting 136 so as to correspond to the time periods for scanning, respectively, one and two of every two frames.

In FIGS. 3, 4 and 6, the spherical lens 1 is fixed and the specimen 7 is moved for scanning in X- and Y-directions. This arrangement is suitable when the specimen is small such as a thin film. When a specimen is larger and a more greater repetitive stress application device is required, however, it becomes impossible to scan the specimen 7 at high speed by the above arrangement. In such a case, the spherical lens may be moved for scanning in X- and Y-directions while the specimen is unmoved so that the repetitive stress is applied to the unmoved specimen. Such a construction produces the same effect as the above-mentioned embodiment by proper synchronization between the movement of the spherical lens 1 and the application of repetitive stress.

It will be understood from the foregoing description that according to the present invention the repetitive stress is applied to a specimen while at the same time observing the processes thereof sequentially, thus permitting detailed observation of the fatigue or tensile rupture of the specimen.

We claim:

1. A method of image display of a specimen by an ultrasonic wave microscope comprising an acoustic wave propagating medium, a piezoelectric member provided at one end of said medium for generating an ultrasonic beam, and an acoustic wave lens formed at an opposite end of said acoustic wave propagating medium and having a predetermined focal point, said method comprising the steps of two-dimensionally scanning a specimen disposed substantially at said focal point by said ultrasonic beam while moving one of said specimen and said beam relative to the other, and applying to said specimen repetitive stress selectively during the scanning of said specimen.

2. A method of image display according to claim 1, wherein repetitive stress is applied to said specimen when said specimen is scanned at other than a predetermined scanning range thereof.

3. A method of image display according to claim 1, wherein said repetitive stress is applied to said specimen when the scanning is carried out for all but one of a predetermined number of image frames in an image display of said specimen.

* * * * *